US011712358B2

(12) United States Patent
Spencer (10) Patent No.: US 11,712,358 B2
(45) Date of Patent: Aug. 1, 2023

(54) ORTHOPEDIC BRACE TO ASSIST WITH SPASTIC GAIT

(71) Applicant: Edwin E. Spencer, Knoxville, TN (US)

(72) Inventor: Edwin E. Spencer, Knoxville, TN (US)

( * ) Notice: Subject to any disclaimer, the term of this patent is extended or adjusted under 35 U.S.C. 154(b) by 336 days.

(21) Appl. No.: 16/877,920

(22) Filed: May 19, 2020

(65) Prior Publication Data

US 2020/0276041 A1 Sep. 3, 2020

Related U.S. Application Data

(63) Continuation-in-part of application No. 15/400,614, filed on Jan. 6, 2017, now Pat. No. 10,653,548.

(60) Provisional application No. 62/275,906, filed on Jan. 7, 2016.

(51) Int. Cl.
*A61F 5/01* (2006.01)
*A61H 3/00* (2006.01)

(52) U.S. Cl.
CPC ............... *A61F 5/01* (2013.01); *A61H 3/00* (2013.01); *A61H 2003/007* (2013.01); *A61H 2201/1207* (2013.01); *A61H 2205/108* (2013.01)

(58) Field of Classification Search
CPC ..... A61B 17/1325; A61B 17/60; A61B 17/62; A61B 17/64; A61F 5/05841; A61F 5/30; A61F 5/05833; A61F 5/0118; A61N 1/205; A61N 2/004; A61N 2/008
See application file for complete search history.

(56) References Cited

U.S. PATENT DOCUMENTS

| 3,421,500 | A | 1/1969 | Jacobson |
| 5,014,981 | A | 5/1991 | Prelich |
| 5,017,185 | A * | 5/1991 | Baermann ................ A61N 2/06 600/15 |
| 5,092,320 | A | 3/1992 | Maurer |
| 5,502,901 | A | 4/1996 | Brown |
| 5,715,539 | A | 2/1998 | Benecki et al. |
| 6,837,862 | B2 | 1/2005 | Driver, Jr. |
| 7,887,462 | B1 | 2/2011 | Bearden |
| 8,057,472 | B2 | 11/2011 | Walker et al. |
| 8,191,180 | B2 | 6/2012 | Berry |
| 8,308,627 | B2 | 11/2012 | Friberg |
| 8,419,734 | B2 | 4/2013 | Walker et al. |
| 10,653,548 | B2 * | 5/2020 | Spencer ................ A61F 5/3715 |

(Continued)

*Primary Examiner* — Ophelia A Hawthorne
(74) *Attorney, Agent, or Firm* — Knox Patents; Thomas A. Kulaga (57) ABSTRACT

Apparatus for an orthopedic brace with magnetic assistance for assisting with a spastic gait. A pair of braces are configured to each support and secure a magnetic device on each leg above the knee. The magnetic devices generate a magnetic force sufficient to reduce a spastic gait. Each magnetic device has a magnetic field that interacts with a magnetic field of the other magnetic device. The magnetic field produces a magnetic force that repels the other magnetic device as the magnetic devices move relative to each other when the wearer walks. The shape of the magnetic field is configured to aid the wearer in avoiding the legs colliding while walking. In one embodiment discrete magnets are disposed on the medial side of each brace. In another embodiment magnetic material is integral with the medial side of each brace and the magnetic material has a selected field strength curve.

13 Claims, 5 Drawing Sheets

(56) References Cited

U.S. PATENT DOCUMENTS

| | | | |
|---|---|---|---|
| 2003/0009077 A1* | 1/2003 | Woo | A61N 2/06 600/15 |
| 2010/0152808 A1 | 6/2010 | Boggs | |
| 2013/0310627 A1* | 11/2013 | Franco | H01F 7/0294 600/15 |
| 2017/0196723 A1 | 7/2017 | Spencer | |

* cited by examiner

ORTHOPEDIC BRACE TO ASSIST WITH SPASTIC GAIT

STATEMENT REGARDING FEDERALLY SPONSORED RESEARCH OR DEVELOPMENT

Not Applicable

BACKGROUND

1. Field of Invention

This invention pertains to an orthopedic brace. More particularly, this invention pertains to a brace with magnetic assistance that aids in allowing a limb to move past a body part.

2. Description of the Related Art

Orthopedic braces are used to address a wide range of musculoskeletal issues. Braces are commonly used to properly align, correct positioning, support, stabilize, and protect certain parts of the body. Braces are often used for acute conditions and injuries, although they are used for chronic conditions. Braces are either dynamic or static, with dynamic braces defined as braces that involve some movement or force as compared to static braces that commonly hold joints in a fixed position and are rigid.

In the art of orthopedic braces, it is known to use magnets. One such device is disclosed in U.S. Pat. No. 6,837,862, by Driver, Jr., issued on Jan. 4, 2005, and titled "Breakaway leg sling." The Driver patent teaches a static brace that holds the knee in flexion with a breakaway safety fastener 93 that uses cooperating magnets. The breakaway safety fastener 93 disengages when a force greater than the magnetic attraction is applied to the fastener 93. Disengagement of the magnetic fastener allows the knee to move out of flexion, such as when the person must straighten the leg to regain balance and prevent a potential fall.

An example of a dynamic brace is disclosed in U.S. Pat. No. 8,191,180, by Berry, issued on Jun. 5, 2012, and titled "Apparatus for preventing head or neck injury using magnetic assistance." The Berry device includes a helmet 12 and shoulder pads 14. The helmet 12 has a magnetic housing 16 that cooperates with a magnetic housing 18 in the shoulder pads 14. The magnetic fields in the two magnetic housings 16, 18 oppose each other, thereby providing a cushioning effect when the helmet 12 is forced backwards.

There are chronic conditions that are aided by wearing an orthopedic brace. Cerebral palsy is one such condition. Cerebral palsy is a neurological disorder that primarily affects body movement and muscle coordination. One form of cerebral palsy is spastic diplegia, which manifests as a tightness or stiffness in the muscles of the lower extremities of the human body, particularly those of the legs, hips, and pelvis. unlike multiple sclerosis, cerebral palsy is not a progressive condition. However, spastic diplegia has symptoms that compound the stresses on the body over time.

Persons with spastic diplegia must work to overcome their stiffness and tightness and to push through that stiffness. Such persons do not have a normal gait pattern when walking. A person with spastic diplegia walks with a spastic gait, often called a scissor gait. With a normal gait, the thighs move past each other without offering any substantial resistance. With a scissors gait, the thighs often rub against each other as one leg moves past the other. The rubbing thighs in the scissors gait impedes walking. The instability in walking with the spastic gait results in undue muscle tension in the upper body, particularly the shoulders, chest, and arms. The extra muscle tension is caused by compensatory stabilization movements of the upper body so that the person maintain balance while walking.

BRIEF SUMMARY

According to one embodiment of the present invention, an orthopedic brace with magnetic assistance is provided. In one such embodiment a pair of braces are configured to fit about the upper legs of a person with a spastic or scissors gait. Each brace has a body and at least one magnetic element or device. The magnetic device of one brace works in cooperation with a magnetic device in the other brace. The magnetic devices produce a magnetic field. The interaction of the magnetic fields produces a magnetic force that repels one brace from the other.

As the person ambulates the two braces move past each other. The magnetic devices cooperate in a manner to correct the specific gait of the person. For example, for one person the magnetic devices first attract then repel as the legs move together then move apart. For another person, the magnetic devices weakly repel as the legs come together and then strongly repel as the legs move apart. In this way the magnetic devices are configured to aid the gait of the person wearing the braces. In yet another embodiment, the magnetic devices have a uniform magnetic field across their surface.

Each brace has a body configured to fit around a leg above the knee. In one embodiment the body includes a carbon fiber sheet that conforms to the shape of the leg. The carbon fiber is light-weight and thin such that the thickness of the braces on the medial side, even with the magnetic elements, is not enough to impede the person ambulating.

In one embodiment, discrete magnets are distributed on the medial side of each brace. In one such embodiment, the location and distribution of the magnets is selected to generate the desired magnetic force for each point in the person's stride to assist in overcoming their spastic gait. In other such embodiments, the magnets are uniformly distributed or distributed in a pre-determined manner. In a second embodiment, the magnetic devices include a magnetized powder that is distributed along the medial face in a manner to produce the desired magnetic force distribution. In various such embodiments, the desired magnetic force distribution is determined to match a gait of a specific person, a standard, pre-determined magnetic field distribution, or a uniform magnetic field distribution.

The problem of minimizing rubbing of a person's thighs against each other while walking with a spastic or scissors gait is solved by each leg having a magnetic device proximate the inner thigh where the magnetic force between the devices on each leg are in opposition and apply a force on the moving leg to minimize contact at the inner thigh.

The problem of tailoring the opposing force between the legs is solved by first measuring the person's gait and then by distributing the magnets on the thigh so as to concentrate the opposing force at the points on the thigh in proportion to the points in the gait that need assistance.

BRIEF DESCRIPTION OF THE SEVERAL VIEWS OF THE DRAWINGS

The above-mentioned features will become more clearly understood from the following detailed description read together with the drawings in which.

DETAILED DESCRIPTION

Apparatus for an orthopedic brace is disclosed. The orthopedic braces are generally indicated as 100, with particular embodiments and variations shown in the figures and described below having an alphabetic suffix, for example, 100-R-A, 100-R-B. Furthermore, left and right elements are designated with a suffix when pertinent, such as when discussing the left support device 106-L and the right support device 106-R, and the left and right designation is omitted when discussing the support device 106 generally.

Figure 1:
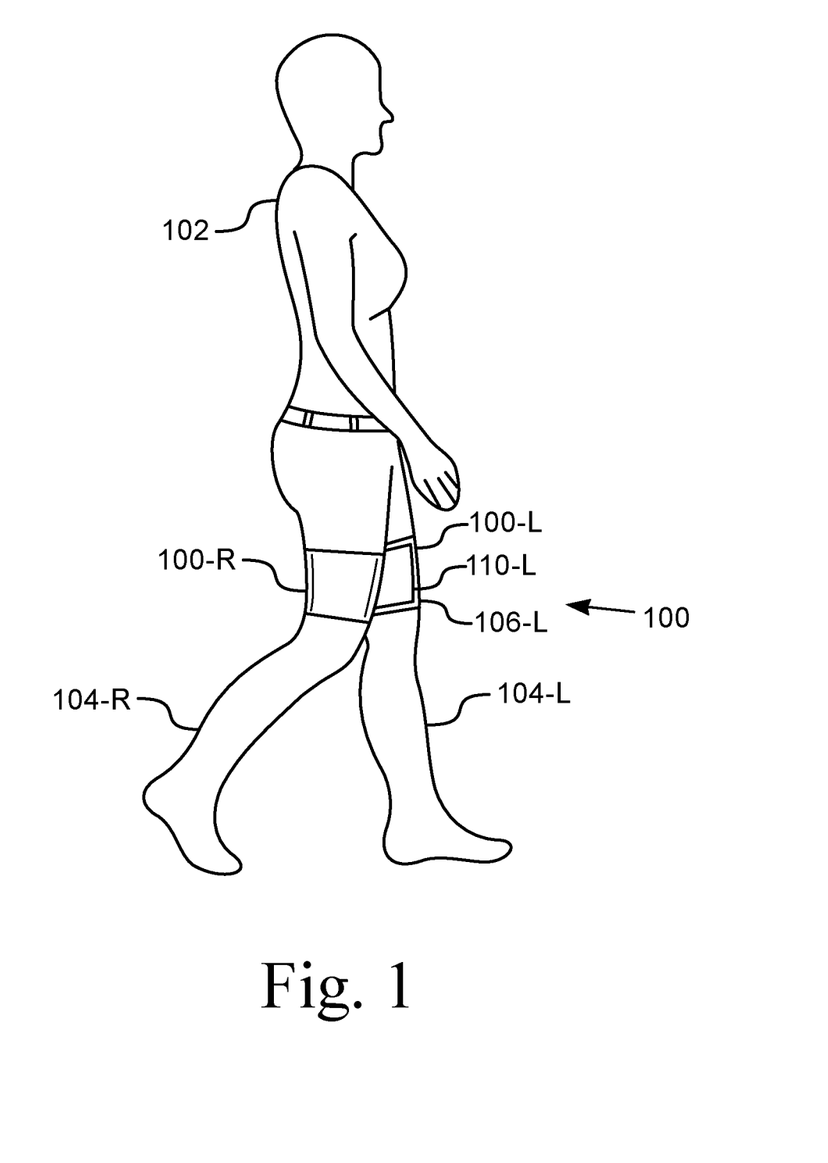
FIG. 1 is a perspective view of a person wearing one embodiment of the braces.

FIG. 1 illustrates a perspective view of a person 102 wearing one embodiment of the braces 100. The person 102 wears a left brace 100-L on the thigh of her left leg 104-L. The braces 100 are worn between the crotch and knee, although the greatest effect is achieved when worn closer to the knee. The person 102 wears a right brace 100-R on the thigh of her right leg 104-R. A person 102 walking with a normal gait moves one foot past the other, one at a time. The person's thighs may brush against each other, but with a normal gait any contact between the thighs does not impede the gait nor the forward motion.

Each brace 100-L, 100-R includes a support device 106 and a magnetic device 110. FIG. 1 illustrates the left brace 100-L with its support device 106-L and magnetic device 110-L visible. In the illustrated embodiment, the support device 106-L fits around the thigh of the person 102. In one embodiment, the support devices 106 are rigid structures that are held in position around the thigh. In another embodiment, the support devices 106 are flexible structures, such as a sleeve that fits around the thigh. In yet another embodiment, the support devices 106 are a combination of rigid and flexible structures, such as where the portion that supports the magnetic device 110 is rigid with a flexible portion extending around the leg 104 and securing the rigid portion in place.

Each of the braces 100 support a magnetic device 110 medial to the corresponding leg 104 proximate the thighs. In the illustrated embodiment, each magnetic device 110 is positioned proximate the medial portion of the brace 100. In one embodiment, each magnetic device 110-L, 110-R extends approximately half-way around the thigh of the person 102. That is, each magnetic device 110-L, 110-R is bounded by the median plane of the associated leg 104-L, 104-R.

Figure 2:
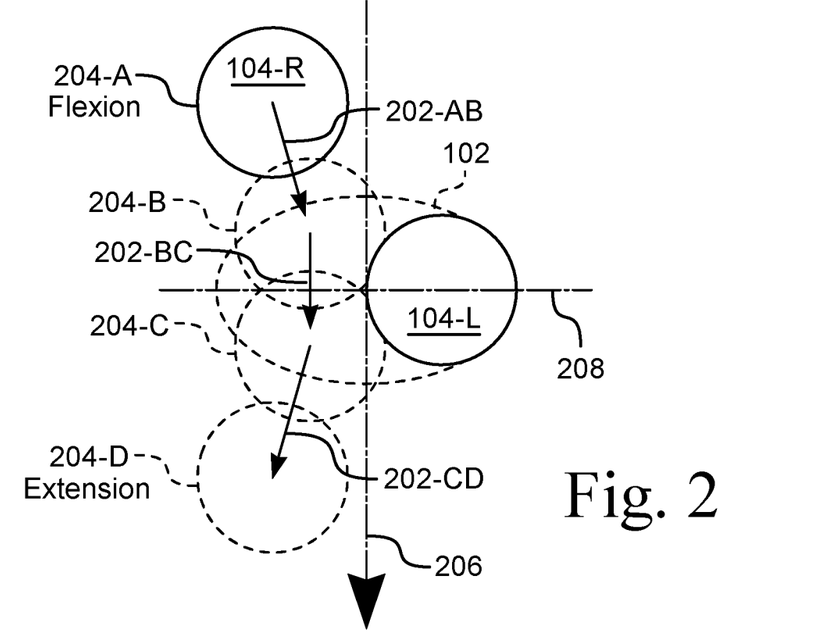
FIG. 2 is a symbolic view of a spastic gait without the aid of the braces.

FIG. 2 illustrates a symbolic view in the transverse plane of a person 102 with a spastic or scissor gait walking a half-step without the aid of the braces 100. A spastic or scissors gait is a gait abnormality primarily associated with spastic diplegia, which is a form of spastic cerebral palsy. Spastic diplegia manifests as a tightness or stiffness in the muscles of the lower extremities of the human body. Often the adductors are out of phase with the quadriceps and hip flexors. Unlike a normal gait where the thighs move past each other without offering any resistance to the forward movement 206, a person 102 with a spastic gait will typically walk with their legs coming close together as they pass, often rubbing against each other and impeding the movement of the leg moving forward.

FIG. 2 illustrates an outline of the torso and mid-thighs of the person 102 with the left leg 104-L stationary and the right leg 104-R taking one step in the forward direction 206. The right leg 104-R moves from the posterior position 204-A to the anterior position 204-D. In the posterior position 204-A the leg 104-R is in flexion. In the anterior position 204-D the leg 104-R is in extension.

The person 102 moves the right leg 104-R forward in direction 202-AB from a first position 204-A to a second position 204-B where the right leg 104-R collides with the left leg 104-L. Depending upon the severity of the person's spastic gait the right leg 104-R drags across the medial surface of the left leg 104-L, either with assistance or under the person's motor control, in a direction 202-BC until the right leg 104-R crosses the medial-lateral plane 208 of the left leg 104-L. When the person's right leg 104-R reaches the third position 204-C the right leg 104-R has cleared the left leg 104-L and moves forward in direction 202-CD to the forward or anterior position 204-D.

Figure 3:
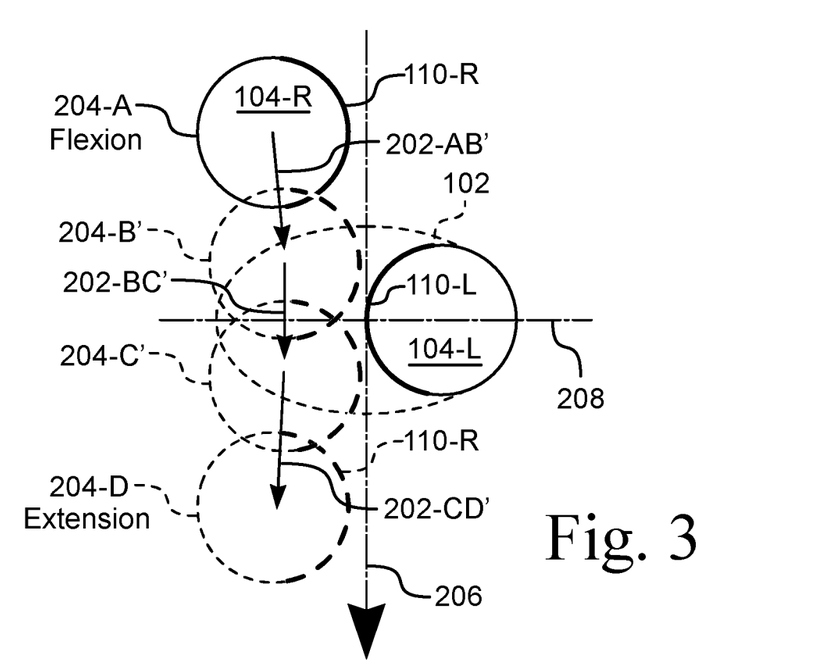
FIG. 3 is a symbolic view in the transverse plane of a spastic gait with the aid of the braces.

FIG. 3 illustrates a symbolic view in the transverse plane of a person 102 with a spastic gait with the aid of the braces 100. The medial thigh portion of the left brace 100-L includes a left magnetic device 110-L, and the medial thigh portion of the right brace 100-R includes a right magnetic device 110-R.

The right leg 104-R starts in a first position 204-A identical to the forth position 204-D shown in FIG. 2. The person 102 moves the right leg 104-R forward in direction 202-AB' from a first position 204-A to a second position 204-B' where the right leg 104-R is spaced apart from the left leg 104-L. The right leg 104-R continues moving in direction 202-BC' without minimal, if any, contact with the left leg 104-L as the right leg 104-R crosses the medial-lateral plane 208 of the left leg 104-L. When the person's right leg 104-R reaches the third position 204-C' the right leg 104-R has cleared the left leg 104-L and moves forward in direction 202-CD' to the forward or anterior position 204-D, which is identical to the forth position 204-D shown in FIG. 2. The spastic gait as shown in FIG. 2 has been corrected so that the person 102 walks more easily in the forward direction 206.

Figure 4:
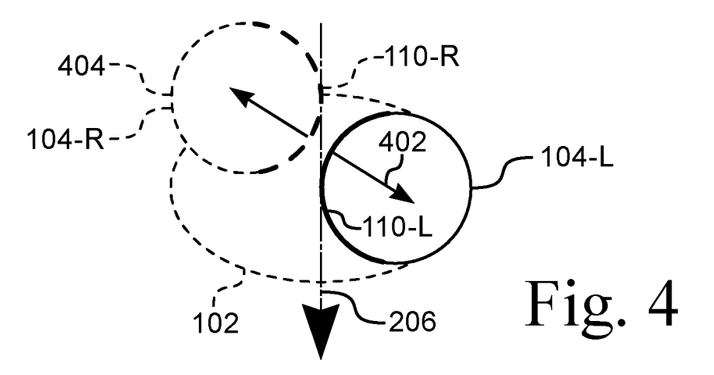
FIG. 4 is a symbolic view in the transverse plane of the magnetic forces at a first position of the moving leg.
Figure 5:
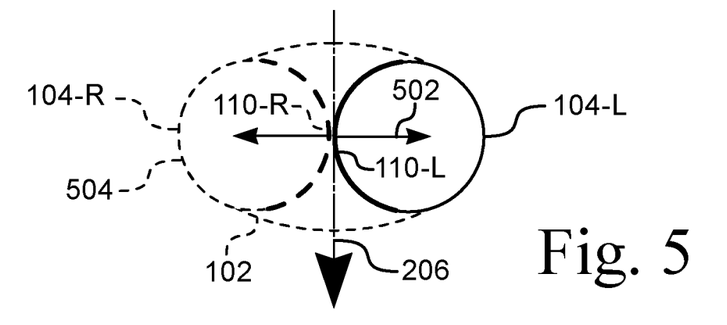
FIG. 5 is a symbolic view in the transverse plane of the magnetic forces at a second, mid position of the moving leg.
Figure 6:
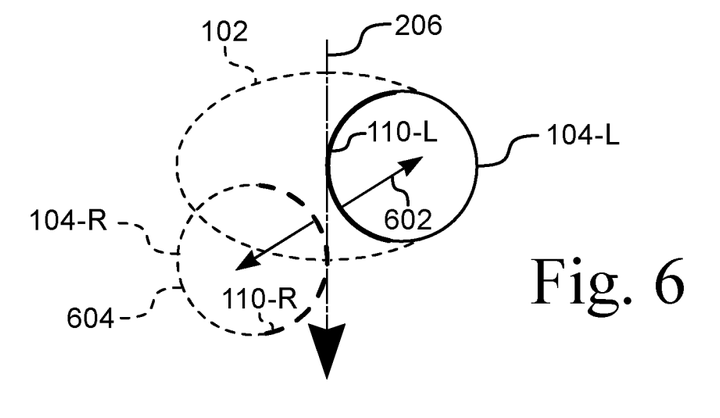
FIG. 6 is a symbolic view in the transverse plane of the magnetic forces at a third position of the moving leg.

FIG. 4 illustrates a symbolic view in the transverse plane of the magnetic forces 402 at a first position 404 of the moving leg 104-R. FIG. 5 illustrates a symbolic view in the transverse plane of the magnetic forces 502 at a second, mid position 504 of the moving leg 104-R. FIG. 6 illustrates a symbolic view in the transverse plane of the magnetic forces 602 at a third position 604 of the moving leg 104-R. The magnetic forces 402, 502, 602 are illustrated as having a direction that tends to move the legs 104-L, 104-R away from each other. That is, the legs 104-L, 104-R are being repelled by each other. The repelling forces 402, 502, 602 aid in alleviating the tendency of a spastic gait to have the legs 104 collide when one passes the other.

The medial thigh portion of the left brace 100-L includes a left magnetic device 110-L, and the medial thigh portion of the right brace 100-R includes a right magnetic device 110-R. In order to produce the magnetic forces 402, 502, 602 that repel the legs 104-L, 104-R, magnetic devices 110-L, 110-R are positioned on each brace 100-L, 100-R. As the legs 104-L, 104-R move relative to each other the magnetic devices 110-L, 110-R interact to produce the desired force.

Figure 7:
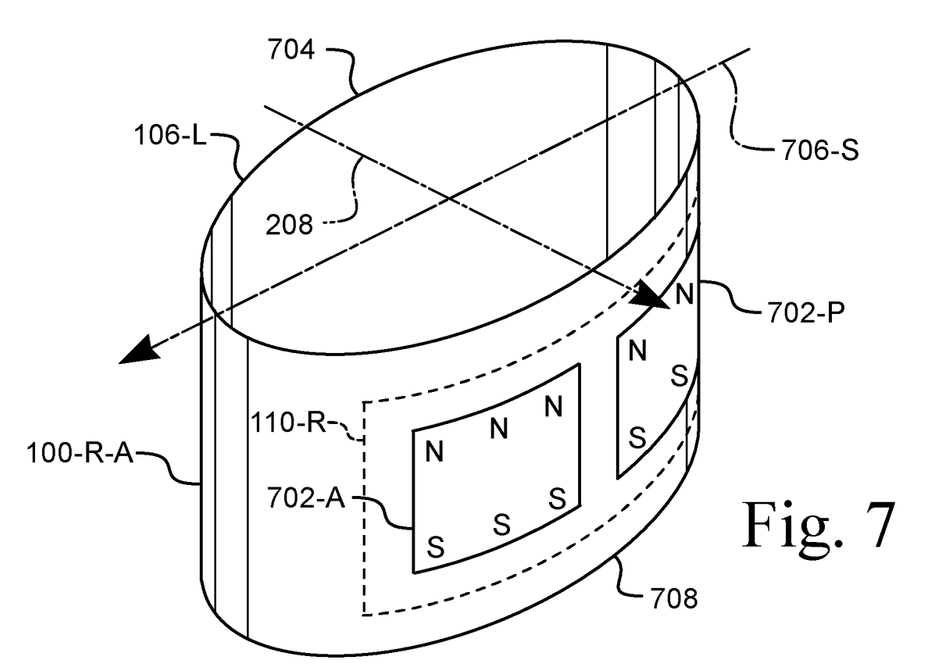
FIG. 7 is an isometric view of one embodiment of a leg brace showing two groups of magnetic elements.
Figure 8:
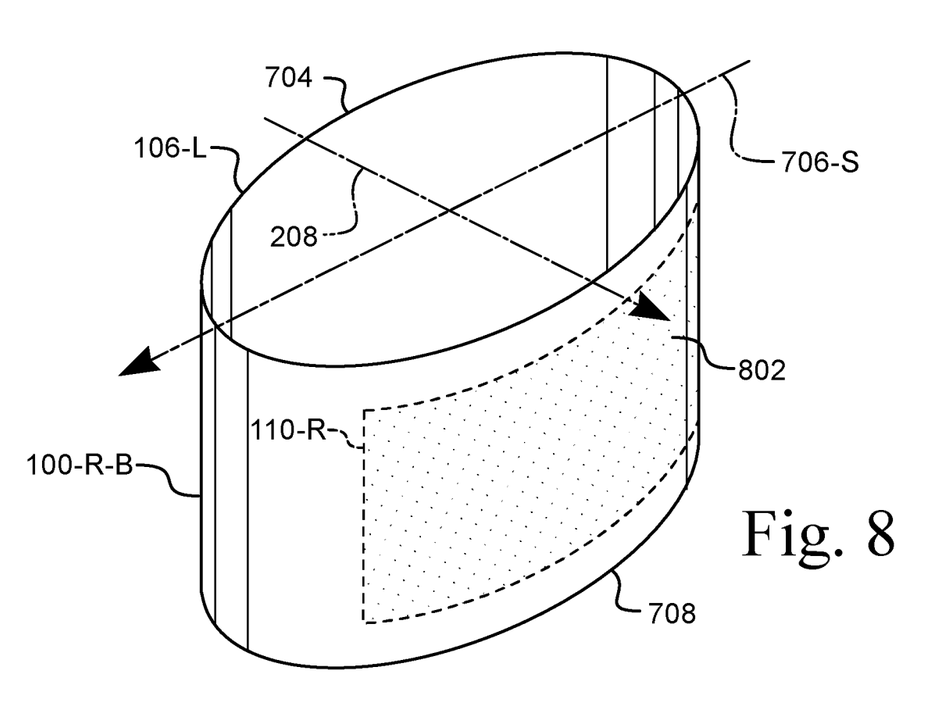
FIG. 8 is an isometric view of another embodiment of one leg brace showing magnetic particles.
Figure 10:
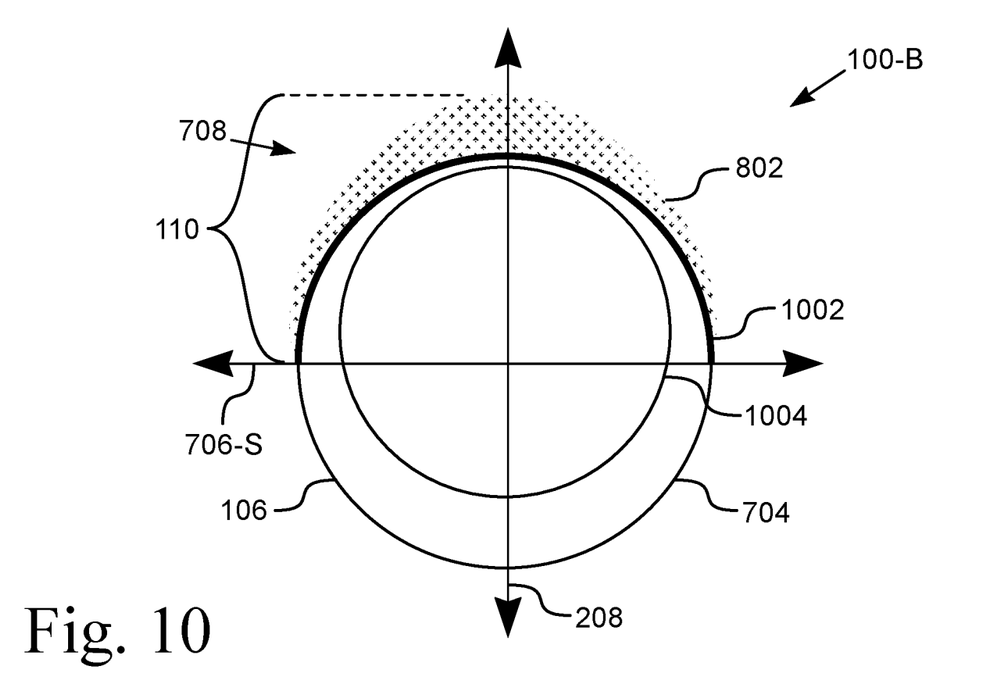
FIG. 10 is a plan view showing the configuration for the curing process of one embodiment of a brace.

The magnetic devices 110-L, 110-R each produce a magnetic field that produces the repelling forces 402, 502, 602. The magnetic fields are produced in various ways. For example, the magnetic devices 110 have permanent magnets 702, such as illustrated in FIG. 7. In another example, the magnetic devices 110 include magnetic particles 802, such as illustrated in FIGS. 8 and 10. In yet another example, the magnetic devices 110 include electromagnetic devices that produce the magnetic fields.

FIG. 7 illustrates an isometric view of one embodiment of a right leg brace 100-R-A showing a magnetic device 110-R that includes two groups of magnetic elements 702-A, 702-P. The corresponding left leg brace 100-L is a mirror image of the right leg brace 100-R-A. The anterior-posterior plane includes a line 706-S that is illustrated as being parallel to the direction 206 of forward movement and is parallel to the sagittal plane of the person 102. The medial-lateral plane 208, illustrated as a line in the figure, bisects the leg 104-R into anterior and posterior halves.

The illustrated brace 100-R-A includes a support device 106 and at least two groups of magnets 702-A, 702-P. The support device 106 includes a brace body 704 configured to fit around the upper leg 104-R of the person 102. The brace body 704 has a medial side 708 that is positioned to interact with a corresponding medial side 708 on the other brace 100. The brace body 704 is sized to fit around the upper thigh of the person 102. In one embodiment the body 704 is a semi-rigid structure formed to the shape of the person's leg 104. For example, a carbon fiber sheet has a shape that fits around the leg 104. In one embodiment the body includes a semi-rigid portion and a flexible portion. The semi-rigid portion supports the magnets 702 and the flexible portion is an elastic or other material that allows the brace 100 to be easily donned, worn, and removed. The body 704 is a thin material, as are the magnets 702. In this way the combined thickness of the body 704 and magnets 702 do not further impede the movement of one leg 104 past the other. The magnets 702 do not protrude or otherwise present a surface that will catch on the other brace 100 as one leg 104 moves past the other.

The brace 100-R-A includes at least groups of magnets 702-A, 702-P. One group of magnets 702-A are positioned anteriorly to the medial-lateral plane 208. The other group of magnets 702-P are positioned posteriorly to the medial-lateral plane 208. In the illustrated embodiment the magnets 702-A, 702-P are arranged such that the poles are symmetrical, that is, the North poles are aligned together. In this way as the two braces 100-L, 100-R come near each other the magnets 702 of one brace 100 repel the magnets 702 of the other brace 100. The magnets 702 are "super magnets" or rare earth magnets, such as those made of neodymium.

In one embodiment, each group of magnets 702-A, 702-P are composed of a single magnet of the desired strength. In one such embodiment the magnets 702-A, 702-P are curved to conform to the shape of the brace 100. In another embodiment, each group of magnets 702-A, 702-P are composed of multiple magnets with a spacing and configuration to produce a desired magnetic force 402, 502, 602 distribution. In such an embodiment the magnets 702-A, 702-P are substantially planar.

Using FIG. 4 as a reference, the anterior magnet 702-A on the right leg brace 100-R-A is nearest the posterior magnet 702-P on the left leg brace 100-L. Because the poles of the magnets 702-A, 702-P are aligned the two sets of magnets 702-A, 702-P repel, thereby applying a repelling force 402 to each brace 100-L, 100-R.

Using FIG. 5 as a reference, the anterior magnet 702-A and the posterior magnet 702-P on the right leg brace 100-R-A are adjacent the anterior magnet 702-A and the posterior magnet 702-P, respectively, on the left leg brace 100-L. In this position the braces 100-L, 100-R are adjacent each other with the medial-lateral planes 208 of each leg 104-L, 104-R aligned. Accordingly, the anterior magnets 702-A oppose each other and the posterior magnets 702-P oppose each other, thereby applying a repelling force 502 to each brace 100-L, 100-R.

Using FIG. 6 as a reference, the posterior magnet 702-P on the right leg brace 100-R-A is nearest the anterior magnet 702-A on the left leg brace 100-L. Because the poles of the magnets 702-A, 702-P are aligned the two sets of magnets 702-A, 702-P repel, thereby applying a repelling force 602 to each brace 100-L, 100-R.

FIG. 8 illustrates an isometric view of another embodiment of a right leg brace 100-R-B showing a magnetic device 110-R that includes magnetic particles 802 embedded in the medial side 708 of the body 704 that interacts with the brace 100-L on the other leg 104. The corresponding left leg brace 100-L is a mirror image of the right leg brace 100-R-B. In the illustrated embodiment the magnet 802 is embedded in the body 704 such that the magnetic force is generated over a broad surface. For example, neodymium powder is distributed along the body 704 on the side that interacts with the other brace 100. The powder 802 is magnetized after it is embedded in the brace body 704. Spreading the neodymium powder across the side of the brace 100-R-B allows the magnetic field 906 to be smoothly distributed along a circumferential length of the brace 100-R-B, thereby avoiding the step change in the magnetic field strength exhibited by discrete magnets 702.

Another method of making a brace 100 such as illustrated in FIG. 8 is with a 3D printer or similar fabrication device. For example, a selective laser sintering (SLS) 3D printer deposits the powder 802 in a desired pattern and shape with the SLS printer sintering the powder 802. In one such example the sintered powder 802 is mated to a brace body 702 and then the powder 802 is magnetized. In this way the sintered powder 802 is pre-fabricated for use with various sized brace bodies 702, thereby accommodating various sizes and configurations of braces 100. In another example the SLS printer forms a substrate with the powder 802 sintered integrally with the substrate. The substrate forms part or all of the brace body 702. In this example the sintered powder 802 is supported and protected for later magnetization and use.

Figure 9:
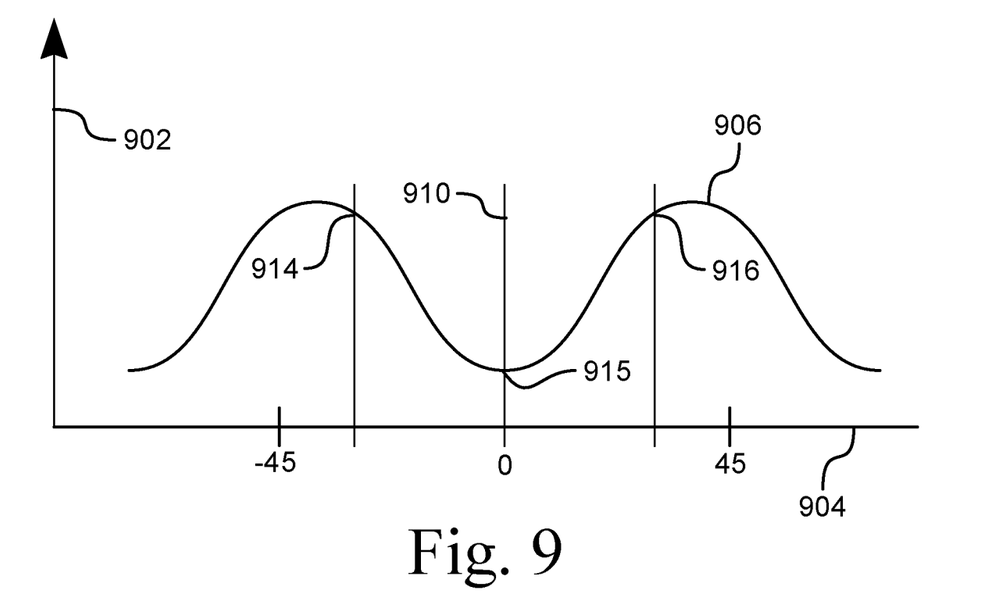
FIG. 9 is a graph showing one embodiment of the magnetic field strength relative to the circumference of the brace.

FIG. 9 illustrates a graph showing one embodiment of a magnetic field strength curve 906 of the magnetic field strength magnitude 902 relative to the circumference 904 of the brace 100. The circumference 904 zero point 910 on the graph of FIG. 9 corresponds to where the medial-lateral plane 208 intersects the medial side 708 of the brace 100. The units on the circumference 904 are in degrees as if the body 704 were cylindrical, which it is not, although it approximates a cylinder.

It bears noting that the illustrated magnetic field strength curve 902 represents the field strength along the surface of the brace 100. The magnetic field strength 902, when considering the distance between the braces 100-L, 100-R, is related to the magnetic force 402, 502, 602 as further described below. Magnetic force varies in accordance with the inverse-square law, that is, magnetic force is inversely proportional to the square of the distance between the two poles.

Using FIG. 4 as a reference, the magnetic field strength 914 corresponding to the first magnetic force 402 is greater than the field strength 502 is at the zero point 910. As one leg 104-R moves forward toward the other leg 104-L, a strong magnetic field 914 is used to generate sufficient magnetic force 402 between the braces 100 to avoid a collision of the legs 104. Using FIG. 5 as a reference, as the leg 104-R moves adjacent the other leg 104-L, the magnetic field strength 915 is reduced. At this position the braces 100 are at their closest and the magnetic field 915 produces a magnetic force 502. The strength of the magnetic force 502, in many cases, is sufficient to prevent the braces 100-L, 100-R from touching. Using FIG. 6 as a reference, the magnetic field strength 916 corresponding to the magnetic force 602 increases.

The shape of the magnetic field strength curve 902 will vary depending upon the particular needs of the person 102 wearing the braces 100. A physical therapist evaluates the gait of the person 102 and determines how much force is necessary to correct the spastic gait at each point in the person's stride. The relationship of force versus stride position is the force profile for that person's gait. The magnetic field strength 902 at each point in the person's stride is determined by the amount of force at that point and the distance between the person's legs 104 at the point where the braces 100 will be worn. After the magnetic field strength curve 902 is determined, the distribution and strength of the magnets 702, 802 is determined. For example, when the curve 902 is asymmetrical, for the embodiment 100-R-A illustrated in FIG. 7, more or stronger magnets 702 are used on one side of the zero point 910 than the other side. For the embodiment 100-R-B illustrated in FIG. 8, the magnetic field strength 902 is precisely tailored by the distribution of the magnetized powder 802.

In one test a magnetic force 402, 502, 602 of approximately four pounds of static force was found to be sufficient to prevent collision of the thighs of a fourteen year old female. The subject female had strong adductors that pulled her legs together as she walked.

The first step in making a brace 100 is to determine the characteristics of the person 102 who will wear the braces 100. This step includes measuring the size of the legs 104 to determine the size of the support device 106. This step also includes evaluating the gait of the person 102 to determine how much force is necessary to correct the spastic gait.

Knowing the characteristics of the person 102, the braces 100 are made by selecting support devices 106 of the appropriate size to fit the person 102 and by selecting magnetic devices 110, each with a magnetic distribution appropriate to the person 102. In the embodiment with the magnetizable powder 802, the powder 802 is magnetized to correspond to the force profile determined for the person 102.

FIG. 10 illustrates a plan view showing the configuration for the curing process of one embodiment of a brace 100-B such as the one shown in FIG. 8. The illustrated embodiment is one example of the process for fabricating a brace 100-B with a desired magnetic field strength curve 906 for the magnetic device 110.

The illustrated support device 106 is a body 704 shown with the magnetic device 110 and a magnetizing mandrel 1004. The magnetic device 110 is shown symbolically as a dispersion of magnetic particles or powder 802 across the substrate 1002. The magnetic particles 802 are embedded in the substrate 1002, which is attached to the body 704. The magnetic device 110 is disposed around approximately one-half of the body 704 on its medial side 708.

The magnetic particles 802 are positioned on the substrate 1002 in a concentration corresponding to the magnetic field strength 902 desired around the magnetic device 110. That is, the portion of the magnetic device 110 where a greater magnetic field strength 902 is desired has a greater concentration of magnetic particles 802 such as shown where the medial-lateral plane 208 bisects the body 704 on the medial side 708. In the example illustrated in FIG. 10, the magnetic field strength curve 906 has a maximum magnetic field strength 902 in the center of the magnetic device 110 and the magnetic field strength 902 decreases in the anterior and posterior directions in the magnetic device 110.

Inside the body 704 is the magnetizing mandrel 1004 that magnetizes the magnetic particles 802 as the substrate 1002 cures. The magnetizing mandrel 1004 is positioned inside the body 704 when the substrate 1002 is being cured. In this way the magnetic particles 802 will be fixed in position on the magnetic device 110-R with the desired magnetic polarity after the substrate 1002 is cured. The magnetic particles 802, in one embodiment, include rare earth elements that are ferromagnetic. As such, the magnetic particles 802 can be permanently magnetized. Additionally, rare earth elements have crystalline structures that are aligned when exposed to a strong magnetic field, such as produced by the magnetizing mandrel 1004.

The process for fixing the desired magnetic field strength curve 906 relative to the body 704 includes the step of positioning the uncured substrate 1002 at the desired location on the body 704. The magnetic particles 802 are distributed across the surface of the substrate 1002 with the desired density for each portion of the magnetic device 110. The magnetic particles 802 mix with the substrate 1002 such that the particles 802 are encapsulated within the substrate 1002. In one embodiment, the magnetic particles 802 are distributed throughout the substrate 1002 with a density such that the resulting magnetic field varies over the surface of each magnetic device 110-L, 110-R with a direct relationship to the density of the particles 802. Such an embodiment is illustrated in FIG. 10 where a large portion of the magnetic particles 802 are concentrated medially with fewer concentrated anteriorly and posteriorly. In another embodiment, the magnetic particles 802 are evenly distributed throughout the substrate 1002 such that the resulting magnetic field is uniform over the surface of each magnetic device 110-L, 110-R. In yet another embodiment, the magnetic particles 802 are distributed throughout the substrate 1002 of each magnetic device 110-L, 110-R such that the magnetic devices 110-L, 110-R have different magnetic field distributions.

After the magnetic particles 802 are embedded in the substrate 1002, the substrate 1002 is cured as the magnetic mandrel 1004 applies a magnetic field to the magnetic device 110. In one embodiment, the substrate 1002 is an epoxy applied to the external surface of the body 704. In such an embodiment, the substrate 1002 is cured by applying heat. The magnetic mandrel 1004 maintains the alignment of the polarity of the magnetic particles 802 as the substrate 1002 cures such that the brace 100-B has a magnetic device 110 with the desired magnetic field strength curve 906.

The braces 100 include various functions. The function of repelling the legs 104-L, 104-R as one passes the other is implemented, in one embodiment, by each magnetic device 110-L, 110-R having a magnetic field orientation that repels the magnetic field of the other magnetic device 110-R, 110-L.

The function of attaching the magnetic devices 110-L, 110-R to the person 102 is implemented, in one embodiment, by a pair of support devices 106-L, 106-R to which the magnetic devices 110-L, 110-R are secured at a desired position on each 104-L, 104-R.

The function of distributing a magnetic field on a pair of magnetic devices 110-L, 110-R is implemented, in one embodiment, by magnetic particles 802 suspended in a substrate 1002, with the density of the magnetic particles 802 directly related to the strength of the magnetic field over a portion of the magnetic devices 110-L, 110-R. In another embodiment, the function of distributing a magnetic field on a pair of magnetic devices 110-L, 110-R is implemented by positioning a plurality of discrete magnets 702 arranged so as to produced the desired magnetic field distribution.

From the foregoing description, it will be recognized by those skilled in the art that braces 100 have been provided. Each brace 100 is configured to fit around a thigh of the person. Each brace 100 includes magnets 702, 802 that are positioned so as to aid the wearer in overcoming a spastic gait. In one embodiment, the person's gait is measured and the magnetic devices are distributed along the brace 100-L, 100-R so as to provide an optimum level of assistance as each leg moves past the other leg when ambulating.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. An apparatus for assisting a person with a spastic gait, said apparatus comprising:
    a first support device dimensioned and configured to fit about a left thigh of the person, said first support device having a first medial side and a first medial-lateral plane;
    a pair of first magnets secured to said first support device, said pair of first magnets including a first anterior magnet and a first posterior magnet, said first anterior magnet positioned anteriorly of where said first medial-lateral plane intersects said first medial side, said first posterior magnet positioned posteriorly of where said first medial-lateral plane intersects said first medial side;
    a second support device dimensioned and configured to fit about a right thigh of the person, said second support device having a second medial side and a second medial-lateral plane; and
    a pair of second magnets secured to said second support device, said pair of second magnets including a second anterior magnet and a second posterior magnet, said second anterior magnet positioned anteriorly of where said second medial-lateral plane intersects said second medial side, said second posterior magnet positioned posteriorly of where said second medial-lateral plane intersects said second medial side;
    whereby said pair of first magnets and said pair of second magnets are oriented such that said pair of first magnets repels said pair of second magnets when said first and second support devices are worn by the person, and a repelling force between said pair of first magnets and said pair of second magnets is sufficient to aid the person in reducing the spastic gait when the person is wearing said first and second support devices.

2. The apparatus of claim 1 wherein said first magnetic field has a first field distribution that varies radially to an axis of said first support device, and said second magnetic field has a second field distribution that varies radially to an axis of said second support device.

3. The apparatus of claim 2 wherein said first and second field distributions correspond to a force profile determined by a gait of the person.

4. The apparatus of claim 2 wherein a first medial location is defined as where said first medial-lateral plane intersects said first medial side and a second medial location is defined as where said second medial-lateral plane intersects said second medial side, said first and second field distributions have a field strength that is stronger at a position anterior to said first medial position than at said first medial position, and said first and second field distributions have a field strength that is stronger at a position posterior to said first medial position than at said first medial position.

5. The apparatus of claim 1 wherein said pair of first magnets opposes said pair of second magnets with sufficient force to prevent said pair of first magnets from contacting said pair of second magnets when the person is walking while wearing said pair of first magnets and said pair of second magnets.

6. The apparatus of claim 1 wherein said first and second support devices are rigid structures that conform to said left and right thighs, respectively.

7. An apparatus for assisting a person with a spastic gait, said apparatus comprising:
    a left brace including a first support device configured to support a first magnetic device at a first position medially on a left thigh of the person; and
    a right brace including a second support device configured to support a second magnetic device at a second position medially on a right thigh of the person, said first magnetic device having a first magnetic field in opposition to a second magnetic field of said second magnetic device when said left and right braces are worn by the person wherein said first magnetic device opposes said second magnetic device with a force sufficient to at least partially correct the spastic gait of the person when the person is wearing said left and right braces.

8. The apparatus of claim 7 wherein said first magnetic device has a first field distribution that varies radially to an axis of said left thigh, and said second magnetic device has a second field distribution that varies radially to an axis of said right thigh.

9. The apparatus of claim 8 wherein said first and second field distributions correspond to a force profile determined by a gait of the person.

10. A method for assisting a person with a spastic gait, said method comprising the steps of:

a) determining a force profile that includes determining a force necessary to correct the spastic gait at a plurality of points in a stride of the person; b) distributing a first magnetic field in a first magnetic device;

c) distributing a second magnetic field in a second magnetic device such that said first magnetic device repels said second magnetic device when first magnetic device is positioned to face said second magnetic device;

c1) step c) includes the step of positioning a plurality of magnets in each of said first and second magnetic devices to so as to generate said force between said first and second magnetic devices when said first and second magnetic devices are placed in positions corresponding to said plurality of points of step a) of determining said force;

d) ensuring said first magnetic device is included with a first support device; and e) ensuring said second magnetic device is included with a second support device.

11. The method of claim 10 further including the steps of f) securing said first magnetic device proximate a medial left thigh of the person and g) securing said second magnetic device proximate a medial right thigh of the person.

12. A method for assisting a person with a spastic gait, said method comprising the steps of:

a) determining a force profile that includes determining a force necessary to correct the spastic gait at a plurality of points in a stride of the person;

b) distributing a first magnetic field in a first magnetic device;

c) distributing a second magnetic field in a second magnetic device such that said first magnetic device repels said second magnetic device when first magnetic device is positioned to face said second magnetic device;

c1) wherein step c) includes the step of magnetizing a powder in a corresponding one of said first and second magnetic devices so as to generate said force between said first and second magnetic devices when said first and second magnetic devices are placed in positions corresponding to said plurality of points of step a) of determining said force;

d) ensuring said first magnetic device is included with a first support device; and e) ensuring said second magnetic device is included with a second support device.

13. The method of claim 12 further including the steps of f) securing said first magnetic device proximate a medial left thigh of the person and g) securing said second magnetic device proximate a medial right thigh of the person.

\* \* \* \* \*